United States Patent [19]

Messroghli et al.

[11] Patent Number: 4,898,157
[45] Date of Patent: Feb. 6, 1990

[54] INSTRUMENT FOR HOLDING SURGICAL NEEDLES

[75] Inventors: Hossein Messroghli, Gross-Gerau; Manfred Boebel, Oetisheim, both of Fed. Rep. of Germany

[73] Assignee: Richard Wolf GmbH, Fed. Rep. of Germany

[21] Appl. No.: 251,750

[22] Filed: Oct. 3, 1988

[30] Foreign Application Priority Data

Oct. 1, 1987 [DE] Fed. Rep. of Germany ....... 3733194

[51] Int. Cl.$^4$ .............................................. A61B 17/04
[52] U.S. Cl. ...................................... 606/147; 81/345; 606/208
[58] Field of Search ........................ 128/321, 322, 340; 81/345, 342

[56] References Cited

U.S. PATENT DOCUMENTS

| | | | |
|---|---|---|---|
| 3,398,746 | 8/1968 | Abramson | 128/340 |
| 4,043,343 | 8/1977 | Williams | 128/321 |
| 4,258,716 | 3/1981 | Sutherland | 128/321 X |
| 4,572,185 | 2/1986 | Rich | 128/321 X |
| 4,644,651 | 2/1987 | Jacobsen | 128/321 X |
| 4,760,848 | 8/1988 | Hasson | 128/321 X |

FOREIGN PATENT DOCUMENTS 8423776 1/1985 Fed. Rep. of Germany .
119702 10/1918 United Kingdom ................ 128/321

*Primary Examiner*—Michael H. Thaler
*Attorney, Agent, or Firm*—Hill, Van Santen, Steadman & Simpson

[57] ABSTRACT

An instrument for holding surgical needles comprises a pair of forceps having forceps jaws at a distal end of the instrument and having a pair of hand grips for operating a movable jaw of the forceps by way of a push and pull rod. The movable jaw is releasably retainable in a closed needle gripping position. The hand grips extend obliquely outwardly in the proximal direction of the instrument and are arranged in mirror image symmetry with respect to the longitudinal axis thereof. The hand grips are actuable in the transverse direction of the longitudinal axis, the forceps jaws, when closed, lying in the direction of that axis. The transverse force exerted on the hand grips is convertable to a longitudinally directed force for actuating the movable jaw, to grip a surgical needle. The instrument can be passed through conventional trocar sleeves.

9 Claims, 2 Drawing Sheets

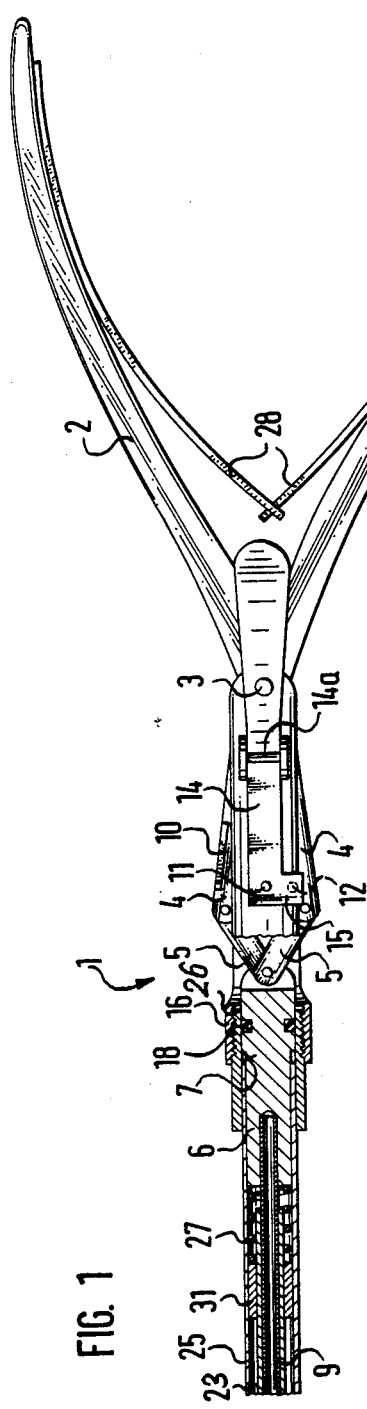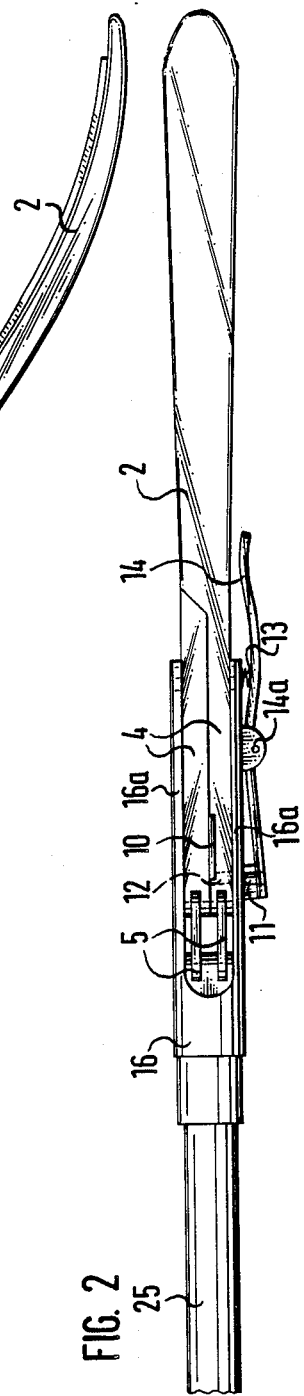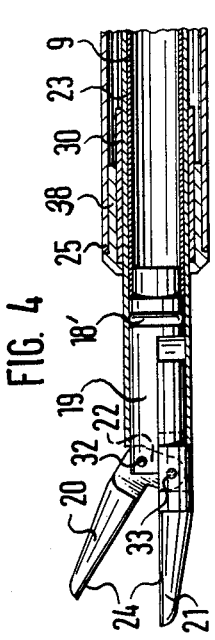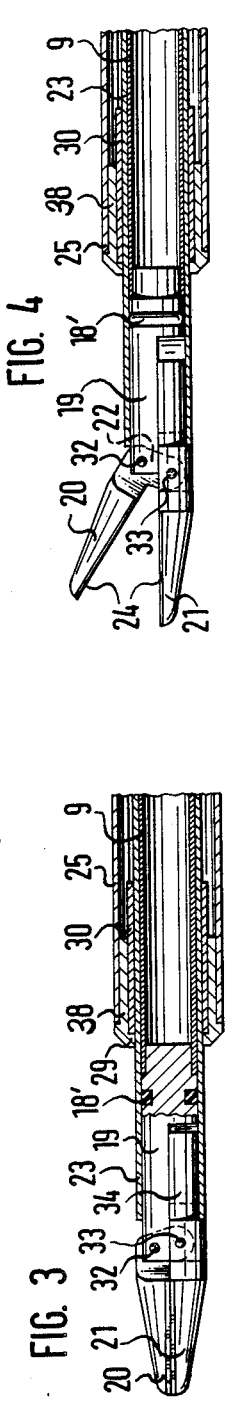

INSTRUMENT FOR HOLDING SURGICAL NEEDLES

FIELD OF THE INVENTION

This invention relates to an instrument for holding surgical needles, which instrument comprises a pair of forceps having forceps jaws at a distal end of the instrument and including a movable forceps jaw which is actuable by means of a handle having two hand grips, by way of push and pull rod means, the movable jaw being releasably lockable in a closed needle gripping position.

BACKGROUND OF THE INVENTION

There is disclosed in German utility model number 8423776, such an instrument for holding surgical needles, in which the jaws are double cranked so that an instrument is usable, in practice, only for endoscopic rectal surgery, since jaws so formed cannot be passed through a conventional trocar sleeve for other endoscopic surgery, especially laparoscopy.

SUMMARY OF THE INVENTION

An object of the invention is to provide an instrument of the kind to which instrument this invention relates, which can be used generally in endoscopic surgery and especially in laparoscopic surgery with the instrument being capable of restraining surgical needles against movement, to the extent necessary in such surgery.

According to the invention therefore, the hand grips extend obliquely outwardly of the instrument and away from its distal end, and are arranged in mirror image symmetry with respect to the longitudinal axis of the instrument. The hand grips are actuable transversely of that longitudinal axis to close the forceps. In the closed position of the forceps, the jaws thereof lie in the direction of said longitudinal axis and the actuating force applied to the hand grips is convertible into a force directed axially of the instrument for actuating the movable jaw to close the forceps.

An instrument according to the invention, can therefore be used generally, in endoscopic surgical procedures, especially in laparoscopy, so that it can be passed through conventional trocar sleeves and the actuating force exerted on the hand grips transversally of the longitudinal axis of the instrument is converted into an axially directed force for closing the forceps.

BRIEF DESCRIPTION OF THE DRAWINGS

FIG. 1 is a plan view shown partly in longitudinal section, of the proximal portion of an instrument for holding surgical needles;

FIG. 2 is side view of FIG. 1;

FIG. 3 is an enlarged longitudinal sectional view through the distal portion of the instrument showing a movable forceps jaw thereof in a closed position, FIG. 3 in conjunction with FIG. 1 showing the whole of the instrument;

FIG. 4 is a similar view to that of FIG. 3 but showing the movable jaw in an open position;

DETAILED DESCRIPTION OF THE INVENTION

Figure 5:
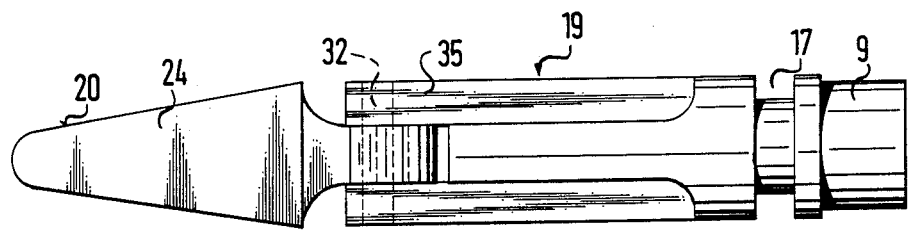
FIG. 5 is an enlarged plan view showing said movable jaw and a push and pull rod to which the jaw is pivotally connected.

As shown in FIG. 1, an instrument 1 for holding surgical needles comprises a handle consisting of a pair of hand grips 2 extending obliquely rightwardly of the instrument in the proximal direction thereof, that is to say outwardly as seen in FIG. 1 and in mirror image symmetry with respect to the longitudinal axis of the instrument 1. The hand grips 2 are pivotally connected by a pivot pin 3, and each hand grip 2 has an extension in the form of lever arm 4 beyond the pin 3 in the distal direction of the instrument, that is to say leftwardly as seen in FIG. 1. Each arm 4 is pivotally connected by way of a guide rod or link 5 to a piston 6 which is displaceable in the direction of said longitudinal axis in order to convert movement of the handle grips 2 about the pin 3, transversally of said longitudinal axis, into movement axially of, that is to say longitudinally of the instrument. The piston 6 is fixedly connected to the proximal end portion 9 of a push and pull rod 9, 19, having a distal end portion 19. The lever arms 4 are each provided with a stop 10, and the stop 10 of one arm 4 comes into abutment with the other arm 4 as the handle grips 2 are pressed towards one another, so as to limit their movement in that direction.

The pin 3 and the arms 4 are mounted to fork arms 16a, best seen in FIG. 2 of a proximal housing part 16 for the piston 6. Mounted between its ends, laterally to the lower (as seen in FIG. 2) arm 16a, at a fulcrum 14a, is a two-armed lever 14 which is swingable manually and which has a locking pin 11 for engagement in a recess 12 in one of the arms 4. As soon as, or shortly before, the arms 4 have been closed towards one another to a maximum extent by moving the handle grips 2 together, the pin 11 is urged into the recess 12 by a spring 13 acting on the lever 14 on the proximal side of the fulcrum 14a, as shown in FIG. 1. The lever 14 has a transverse angled portion 15 which is supported on one of the arms 4 so that pin 11 cannot engage between the arms 4. When the hand grips 2 are actuated to close a movable forceps jaw 20 of the instrument against a fixed forceps jaw 21, thereof, as described below, by pressing the hand grips together, engagement of the pin 22 in the recess 12 secures both the hand grips 2 and the jaw 20 in a forceps closure position. The pin 11 can be withdrawn from the recess 12 by pressing manually on the proximal end portion of the lever 14.

An outer housing, which is provided for the piston 6 and the push and pull rod 9, 19, consists of the housing part 16, an outer hollow shaft 25 and an inner hollow shaft 23 which are securely connected together. The diameter of the shaft 25 in the transverse direction of said longitudinal axis is greater than the diameter of forceps jaws 20, 21 when the movable jaw 20 has been closed against the fixed jaw 21. The shaft 25 is spaced at 7 (see FIG. 1) from a step formed in the piston 6, when the jaw 20 is in its open position. The piston 6 is therefore displaceable in the distal direction as the handle grips 2 are pressed together to close the jaw 20.

Figure 7:
FIG. 7 is an enlarged side view of a fixed jaw of the instrument.
Figure 8:
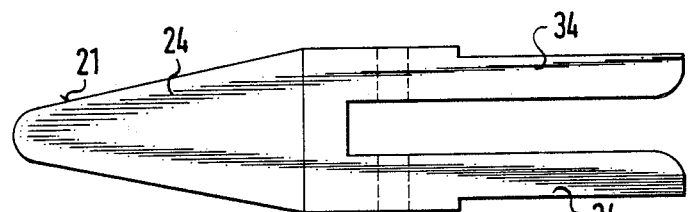
FIG. 8 is a top plan view of the fixed jaw.

The forceps jaws 20 and 21, which have inner, needle gripping surfaces 24, are, as best seen in FIGS. 3 and 4, provided at the distal end of the instrument 1. The jaw 21, which as mentioned above is fixed, is connected rigidly and securely to the inner shaft 23 by means of fork-like extensions 34 (FIGS. 3, 7 and 8) of the jaw 21. The jaw 20, which is movable as mentioned above, has a angled portion 22 which is pivotally mounted to the jaw 21 to allow the jaw 20 to swing about a pivot pin 33 relative to the jaw 21. The angled portion 22 is pivotally connected also to the distal end portion 19 of the push and pull rod 9, 19, by means of a pivot pin 32.

Figure 6:
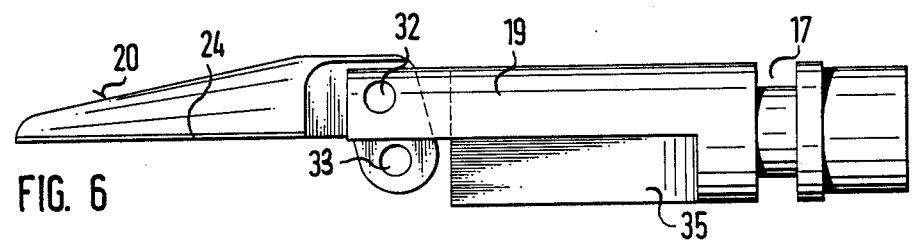
FIG. 6 is a side view of FIG. 5.

The piston 6 to which the rod 9, 19 is connected, is sealed in the housing part 16, by means of a sealing ring 18 as shown in FIG. 1, an identical sealing ring 18 in a groove 17 (FIG. 4 and 6) between the distal end portion 19 and the proximal end portion 9 of the rod 9, 19 seals the latter in the shaft 23. For receiving the fork-like extensions 34 of the fixed jaw 21, the distal end portion 19 of the push and pull rod 9, 19 is provided with recesses 35 in which the extensions 34 engage (FIG. 5).

In order to retain the movable jaw 20 in its unactuated initial angular position in which it is spaced from the fixed jaw 21, a compression spring 27 is provided between a cylindrical sleeve 31, which is intermediate the shafts 23 and 25 and is fixed to the inner shaft 23, and the piston 6 on the proximal portion 9 of the push and pull rod 9, 19. A spring 28 (FIG. 1) is also provided for urging the hand grips 2 apart from one another.

Adjustment of the force to be applied to a surgical needle (not shown) to be gripped between the surfaces 24 of the jaws 20 and 21 is effected, after the pivot pins 32 and 33 have been assembled, but before non-detachably assembling the shaft 23 to the shaft 25 and non-detachably assembling of the shaft 25 to the housing part 16. Since the compression spring 27 is supported in the distal direction, both in the unactuated, initial position of the jaw 20 and in the actuated position thereof, against the sleeve 31 secured to the shaft 23, a shoulder 29 on an internal sleeve 38 fixed in the shaft 25 provides an abutment for a cylindrical sleeve 30 non-detachably secured to the shaft 23 towards its distal end. The angular position of the shoulder 29 can be adjusted by rotating the outer shaft 25 in the housing part 16. If in the unactuated position of the jaw 20, the shaft 25 is screwed deeper into the housing 16, the shaft 23, to which the fixed jaw 21 is secured, is displaced in the proximal direction by the shoulder 29 acting on the sleeve 30, against the action of the spring 27, so that the jaw 20, which is in its open, that is to say its unactuated, position, is swung through a predetermined angle towards the fixed jaw 21. If the hand grips 2 are now actuated by pressing them toward one another against the action of the springs 27 and 28, the push and pull rod 9, 19 is displaced in the distal direction and the jaw 20 is thereby swung towards the stationary jaw 21. The adjustment of the pressure that the surfaces 24 of the jaws 20 and 21 exert against the needle, is effected by rotating the shaft 25 relative to the housing 16 by ways of a threaded connection 26 between them, gradually, until the required clamping pressure of the jaws 20 and 21 on the needle is achieved.

In order to avoid damage to the hinged parts of the instrument 1 in particular of the pivot pins 32 and 33, by improper adjustment by the user, the shafts 23 and 25 are secured together undetachably and shaft 25 is secured to the housing 16 undetachably, after the clamping pressure of the jaws 20 and 21 against the needle, has been adjusted as aforesaid.

The jaws 20 and 22, are secured together by means of the pivot pins 32 and 33 with a predetermined spacing, so that the needle gripping inner surfaces 24 of the jaws 20 and 21 act upon the surface of the needle almost perpendicularly to the longitudinally axis of the instrument 1.

What is claimed is:
1. An instrument for holding surgical needles, said instrument having a distal end, a proximal end, and a longitudinal axis, the instrument comprising: an elongated member extending along said longitudinal axis, a pair of forceps having forceps jaws at said distal end including a fixed jaw on a distal end of said elongated member, a movable jaw pivotably mounted on said fixed jaw, a push and pull rod being connected to the movable jaw, a handle having a pair of hand grips being pivotably connected to the proximal end of said elongated member and extending obliquely outwardly of the instrument in the proximal direction thereof and being arranged in mirror image symmetry with respect to said longitudinal axis; the hand grips being actuatable by an actuating force exerted thereon transversly of said axis to move both hand grips toward the longitudinal axis to bring the forceps to said closed position with the forceps jaws lying in the direction of said longitudinal axis, connecting means connected to a distal end of said hand grips and a proximal end of said rod for converting the actuating force into a force directed longitudinally to the instrument to shift the rod to actuate the movable jaw, and means for releasably locking said movable jaw in its actuated position.

2. An instrument according to claim 1, which includes an outer housing receiving said forceps and having a diameter which is greater than that of said jaws in said closed position in the transverse direction of said longitudinal axis.

3. An instrument according to claim 1, wherein the means for releasably locking includes the hand grips having extensions which are secured together by means of a pin engaging in one of the extensions in the actuated position of the movable jaw, the pin being arranged on a two-armed lever which is biased to engage the pin in said one extension, said lever being movable manually to disengage the pin therefrom.

4. An instrument according to claim 3, wherein the said one extension lies beyond a pivotal axis of the hand grips and is provided with a transverse recess in which the pin is engagable, the two-armed lever having an offset position for abutting against said one extension.

5. An instrument according to claim 1, wherein said connecting means includes a piston connected to said rod and a pair of links connecting said piston to the distal ends of said pair of hand grips.

6. An instrument according to claim 1, wherein said movable jaw has a transverse arm at a proximal end, said arm being pivotably connected to said fixed jaw and said proximal end being connected to said rod.

7. An instrument according to claim 1, wherein said connecting means includes a piston connected to the rod and to each of the hand grips, and a spring acting as said piston to urge the hand grips apart.

8. An instrument for holding surgical needles, said instrument having a distal end, a proximal end, and a longitudinal axis, the instrument comprising: an elongated tubular member; a pair of forceps jaws including a fixed jaw mounted on a distal end of said member, a movable forceps jaw being pivotably mounted to said fixed jaw; a push and pull rod extending through said member and being connected to the movable jaw; a piston connected to a proximal end of said rod and being received in said proximal end of said tubular member; a handle having a pair of hand grips being pivotably connected to said proximal end of said member and the hand grips extending obliquely outwardly of the instrument in the proximal direction thereof and being arranged in mirror image symmetry with respect to said longitudinal axis, the hand grips being actuatable by an actuating force exerted thereon transversely of said axis to move both hand grips toward the longitudinal axis to bring the forceps to said closed position with the forceps jaws lying in the direction of said longitudinal axis; means including a pair of links extending between the piston and said pair of hand grips for converting the actuating force into a force directed longitudinally to the instrument to shift the rod to actuate the movable jaw; and means for releasably locking said movable jaw in its actuated position.

9. An instrument according to claim 8, wherein said means for locking includes a lever having a pin at one end, said lever being mounted for pivotable movement adjacent said hand grips, a spring acting on said lever to urge said pin into engagement with one of the hand grips to lock the hand grips in a position to hold the movable jaw in the actuated position.

* * * * *